US012629098B2

(12) United States Patent
Huang et al.

(10) Patent No.: US 12,629,098 B2
(45) Date of Patent: *May 19, 2026

(54) SIGNAL SENSING DEVICE WITH SIGNAL MAGNIFYING STRUCTURE

(71) Applicant: METAL INDUSTRIES RESEARCH & DEVELOPMENT CENTRE, Kaohsiung City (TW)

(72) Inventors: Shu-Hung Huang, Kaohsiung City (TW); Chun-Chieh Tseng, Kaohsiung City (TW); Jui-Han Lu, Kaohsiung City (TW); Chun-Ming Chen, Kaohsiung City (TW); Ping-Ruey Chou, New Taipei City (TW); Yen-Hsin Kuo, Kaohsiung City (TW); Tung-Lin Tsai, Tainan City (TW); Yen-Hao Chang, Kaohsiung City (TW); Sheng-Hua Wu, Kaohsiung City (TW); Chia-Hua Chang, Kaohsiung City (TW); Wen-Ming Cheng, Kaohsiung City (TW)

(73) Assignee: Metal Industries Research & Development Centre, Kaohsiung City (TW)

( * ) Notice: Subject to any disclaimer, the term of this patent is extended or adjusted under 35 U.S.C. 154(b) by 242 days.

This patent is subject to a terminal disclaimer.

(21) Appl. No.: 18/498,608

(22) Filed: Oct. 31, 2023

(65) Prior Publication Data

US 2025/0134468 A1     May 1, 2025

(51) Int. Cl.
*A61B 5/00* (2006.01)
*A61B 5/026* (2006.01)

(52) U.S. Cl.
CPC .......... *A61B 5/7225* (2013.01); *A61B 5/6847* (2013.01)

(58) Field of Classification Search
CPC ....... A61B 5/7225; A61B 5/6847; A61B 5/07; H01Q 1/273
See application file for complete search history.

(56) References Cited

U.S. PATENT DOCUMENTS 12,355,143 B2 * 7/2025 Huang ................... H01Q 1/273
2007/0015984 A1 * 1/2007 Yeo ........................ A61B 5/259
600/372

(Continued)

*Primary Examiner* — Carl H Layno
*Assistant Examiner* — Anh-Khoa N Dinh
(74) *Attorney, Agent, or Firm* — WPAT, PC

(57) ABSTRACT

A signal sensing device includes a signal amplifying structure to amplify the strength of the measured signal. The signal sensing device includes a body, a signal sensing element, and a signal amplifying portion. The signal sensing element is disposed in the body and includes a signal transmission section and a signal sensing section in electrical connection with the signal transmission section. The signal amplifying portion includes a plurality of protruding structures protruding outward from the body. Each of the plurality of protruding structures is cylindrical and has a diameter of 250-400 μm and a height of 40-75 μm. When a portion of the body forms a surrounding portion surrounding a to-be-sensed target, a portion or an entirety of the signal sensing section is located on the surrounding portion, and the signal amplifying portion is partially or entirely in contact with the to-be-sensed target.

16 Claims, 6 Drawing Sheets

(56) References Cited

U.S. PATENT DOCUMENTS

| 2016/0120432 | A1* | 5/2016 | Sridhar | A61B 5/6898 |
| | | | | 600/544 |
| 2018/0192911 | A1* | 7/2018 | Jung | A61B 5/0531 |
| 2021/0378572 | A1* | 12/2021 | Beker | A61B 5/0535 |
| 2024/0180492 | A1 | 6/2024 | Tseng et al. | |

* cited by examiner

SIGNAL SENSING DEVICE WITH SIGNAL MAGNIFYING STRUCTURE

BACKGROUND OF THE INVENTION

1. Field of the Invention

The present invention relates to a signal sensing device and, more particularly, to a signal sensing device with a signal magnifying structure.

2. Description of the Related Art

In a conventional method of proceeding with signal measurements by surrounding a to-be-measured target, such as an organ or a tissue of an organism, since there are many interfering sources inside or outside of the organism during measurement of the target signals of the to-be-measured target, the target signals are too weak or include excessive noise signals, such that the measured target signals are distorted or inaccurate, leading to deviations or errors in subsequent analysis, judgment, or reading on the measured target signals.

In light of the above, it is necessary to improve the conventional signal sensing device.

SUMMARY OF THE INVENTION

To solve the above problems, it is an objective of the present invention to provide a signal sensing device capable of enhancing the strength of the sensing signal.

It is another objective of the present invention to provide a signal sensing device suitable for sensing signals of a specific internal organ or tissue of an organism, particularly the signals of blood vessels.

It is a further objective of the present invention to provide a signal sensing device which can be mounted inside an organism and can be degraded and absorbed by the organism as time passes.

As used herein, the term "a", "an" or "one" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

The dimensional definitions related to sizes recited herein are based on FIG. 1 of the accompanying drawings. The term "length" refers to the extending direction of the length (designated by $L_H$ or $L_E$) of the head portion or the extension portion of the body, which is the extending direction of Y axis of FIG. 1. The term "width" refers to the extending direction of the width (designated by $W_H$ or $W_E$) of the head portion or the extension portion of the body, which is the extending direction of X axis of FIG. 1. The term "thickness" (or "height") refers to the extending direction of the thickness (designated by $T_H$ or $T_E$) of the head portion or the extension portion of the body, which is the extending direction of Z axis of FIG. 1. Furthermore, the size referred to herein may be adjusted by 0.1 μm per adjustment. Furthermore, the "working frequency" referred to herein may be adjusted by 1 MHz per adjustment. Furthermore, the numerical value mentioned herein may have a tolerance of ±10%.

A signal sensing device according to the present invention includes a body, a signal sensing element, and a signal amplifying portion. The signal sensing element is disposed in the body and includes a signal transmission section and a signal sensing section in electrical connection with the signal transmission section. The signal amplifying portion has a plurality of protruding structures protruding outward from the body. Each of the plurality of protruding structures is cylindrical and has a diameter of 250-400 μm, preferably 300-350 μm, and a height of 40-75 μm, preferably 50 μm. When a portion of the body forms a surrounding portion surrounding a to-be-sensed target, a portion or an entirety of the signal sensing section is located on the surrounding portion, and the signal amplifying portion is partially or entirely in contact with the to-be-sensed target.

Therefore, by the disposition of the above specific shape and size of the protruding structures of the signal sensing element according to the present invention, when the signal sensing device is disposed around the to-be-sensed target to proceed with signal sensing, the strength of the sensing signal can be enhanced significantly.

In an example, the body includes a head portion and an extension portion connected to the head portion. The extension portion extends outward from an end of the head portion and has a length to surround the to-be-sensed target by an entirety or a portion of the extension portion. Therefore, by the disposition of the head portion and the extension portion, the signal sensing device is suitable for disposition surrounding a to-be-sensed target.

In an example, the signal transmission section is disposed on the head portion of the body and includes an antenna structure. The signal sensing section is disposed on the extension portion of the body. The signal amplifying portion protrudes from the extension portion of the body and is aligned with the signal sensing section of the signal sensing element. Therefore, by the disposition of the signal transmission section and the signal sensing section respectively corresponding to the head portion and the extension portion, the structures of the signal sensing device for the transmission function and the sensing function are properly disposed to avoid mutual interference between the transmission signal and the sensing signal. Furthermore, by the disposition of the magnifying portion aligned with the extension portion and the signal sensing section, when the signal sensing device is disposed to surround the to-be-sensed target for signal measurement, the strength of the sensing signal can be enhanced significantly.

In an example, the head portion of the body has a length and a width both of which are 5-35 mm. The extension portion has a width of 2-15 mm. Each of the head portion and the extension portion has a thickness of 50-350 μm. Each of the signal transmission section and the signal sensing section has a thickness of 10-100 μm. Therefore, by the disposition of the above sizes, the signal sensing device may be suitable for a specific environment having a limited space (such as the anterior of a human, a rabbit, or a mouse, or the interior of a larger organism) and for sensing signals associated with a specific to-be-sensed target (such as an organ or a tissue).

In an example, both the length and the width of the head portion of the body are 10-30 mm, and the width of the extension portion is 5-10 mm. Therefore, by the disposition of the above sizes, the signal sensing device is suitable for use in a specific environment having a limited space to proceed with sensing of signals of a to-be-sensed target.

In an example, both the length and the width of the head portion of the body are 15-20 mm. Therefore, by the disposition of the above sizes, the signal sensing device is suitable for use in a specific environment having a limited space to proceed with sensing of signals of a to-be-sensed target.

In an example, the body further includes an assembling structure having a first assembling portion and a second assembling portion which are spaced from each other and which are disposed on the body. When the portion of the body forms the surrounding portion, the first assembling portion and the second assembling portion are aligned with each other. Therefore, by the alignment of the first assembling portion and the second assembling portion, a fastener may be used to conveniently and easily engage with the assembling structure, thereby simply and conveniently installing the signal sensing device onto the to-be-sensed target.

In an example, the signal sensing device further includes a fastener. When the first assembling portion and the second assembling portion are aligned with each other, the fastener is engaged with the first assembling portion and the second engaging portion to maintain the shape of the surrounding portion. Therefore, by engaging the fastener with the assembling structure, the signal sensing device may be fixed to the to-be-sensed target.

In an example, each of the first assembling portion and the second assembling portion includes at least one through-hole. The fastener includes a connecting portion, at least one insertion portion, and at least one engaging portion. The at least one insertion portion protrudes outward from the connecting portion. The at least one engaging portion protrudes outward from the at least one insertion portion. When the fastener is engaged with the first assembling portion and the second assembling portion, the at least one insertion portion extends through aligned through-holes of the first assembling portion and the second assembling portion, the connecting portion is located on a side of one of the first assembling portion and the second assembling portion, and the at least one engaging portion engages with and abuts against a side of another of the first assembling portion and the second assembling portion. Therefore, by the disposition of the fastener and the assembling structure, the fastener and the assembling structure have a simple structure to fix the signal sensing device on the to-be-sensed target.

In an example, the at least one through-hole of each of the first assembling portion and the second assembling portion has a diameter in a radial direction. The at least one engaging portion includes an inlet end and an engaging end. The inlet end is opposite to the connecting portion. The engaging end is located between the connecting portion and the inlet end. The inlet end expands gradually towards the engaging end, such that the at least one engaging portion has gradually increasing lengths in the radial direction from the inlet end towards the engaging end in an axial direction perpendicular to the radial direction. Therefore, by the disposition of the gradually expanding shape of the engaging portion of the fastener, easy engagement with the assembling structure can be achieved easily while achieving secure engagement between the fastener and the assembling structure.

In an example, each of the first assembling portion and the second assembling portion has two through-holes, and the fastener includes two insertion portions, with the number of the insertion portions being in association with the number of the through-holes, such that the fastener is substantially U-shaped or V-shaped. Therefore, by providing the assembling structure with two through-holes for assembly and with the fastener having a corresponding number of insertion portions, in comparison with the case of only one through-hole and only one insertion portion, the force imparted to the fixture and the assembling structure is more uniform, thereby enhancing the engagement stability between the fastener and the assembling structure. Furthermore, in comparison with the case having more than two through-holes and more than two insertion portions, the overall structure may be used in a compact space, and the shapes of the fastener and the assembling structure are simpler, permitting easy manufacturing and saving the manufacturing costs.

In an example, the body further includes a plurality of marked features disposed on the body and aligned with the first assembling portion and the second assembling portion. Therefore, easy alignment of the assembling structure can be improved during installation.

In an example, each of the plurality of marked features is a triangular notch having a vertex aligned with an associated one of the first assembling portion and the second assembling portion. Therefore, easy alignment of the assembling structure can be improved during installation.

In an example, each of the plurality of marked features is a line-type mark. Therefore, easy alignment of the assembling structure can be improved during installation.

In an example, the signal sensing device is made of one or more bio-degradable materials. Therefore, the signal sensing device according to the present invention is suitable for installation in an organism to sense the interested signals and can degrade completely in a predetermined period of time without the need of removal by operation, thereby avoiding the risk caused by the second operation.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
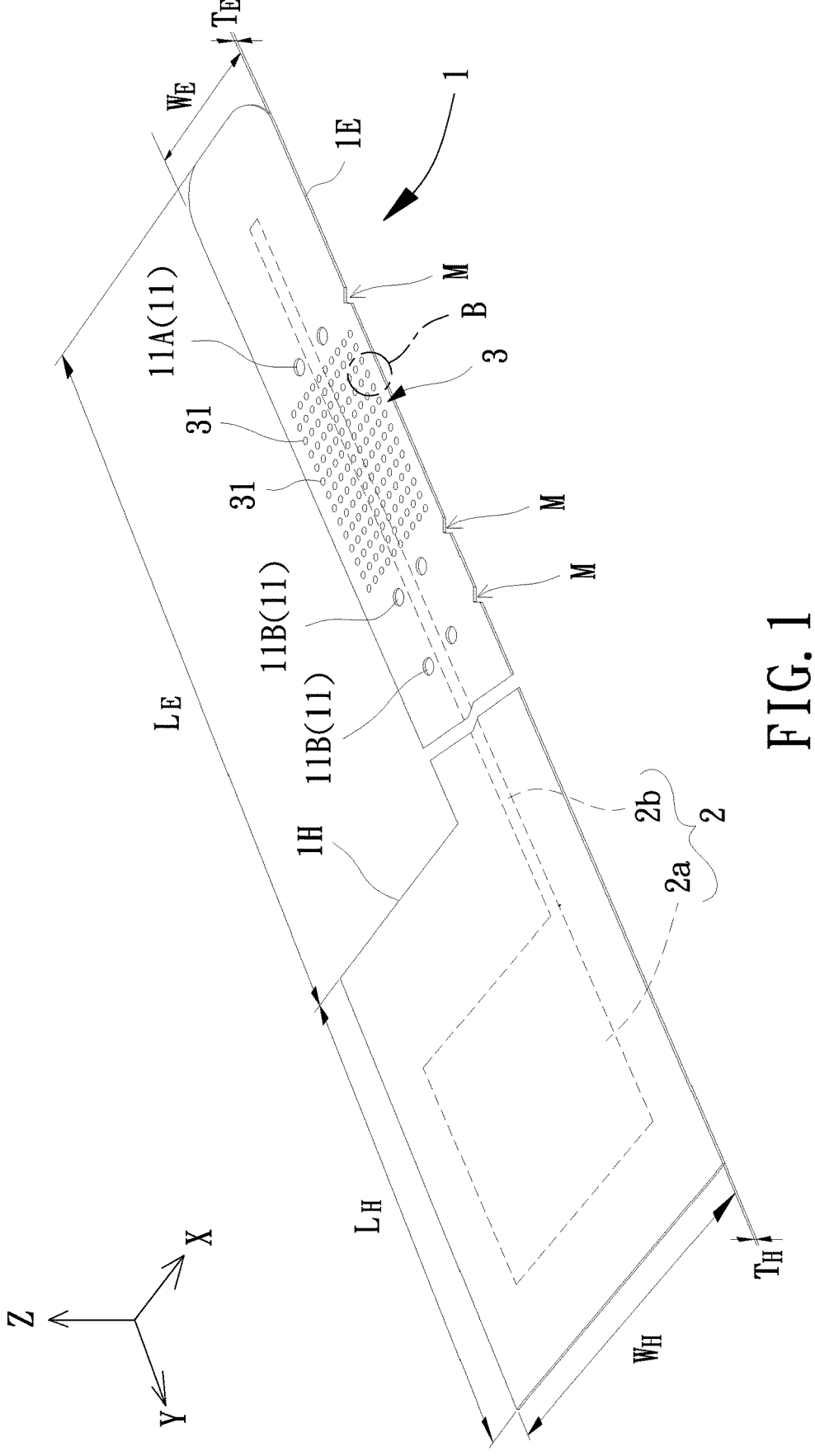
FIG. 1 is a diagrammatic perspective view of a signal sensing device of a preferred embodiment according to the present invention.

When the terms "front", "rear", "left", "right", "up", "down", "top", "bottom", "inner", "outer", "side", and similar terms are used herein, it should be understood that these terms have reference only to the structure shown in the drawings as it would appear to a person viewing the drawings and are utilized only to facilitate describing the invention, rather than restricting the invention.

DETAILED DESCRIPTION OF THE INVENTION

Figure 2:
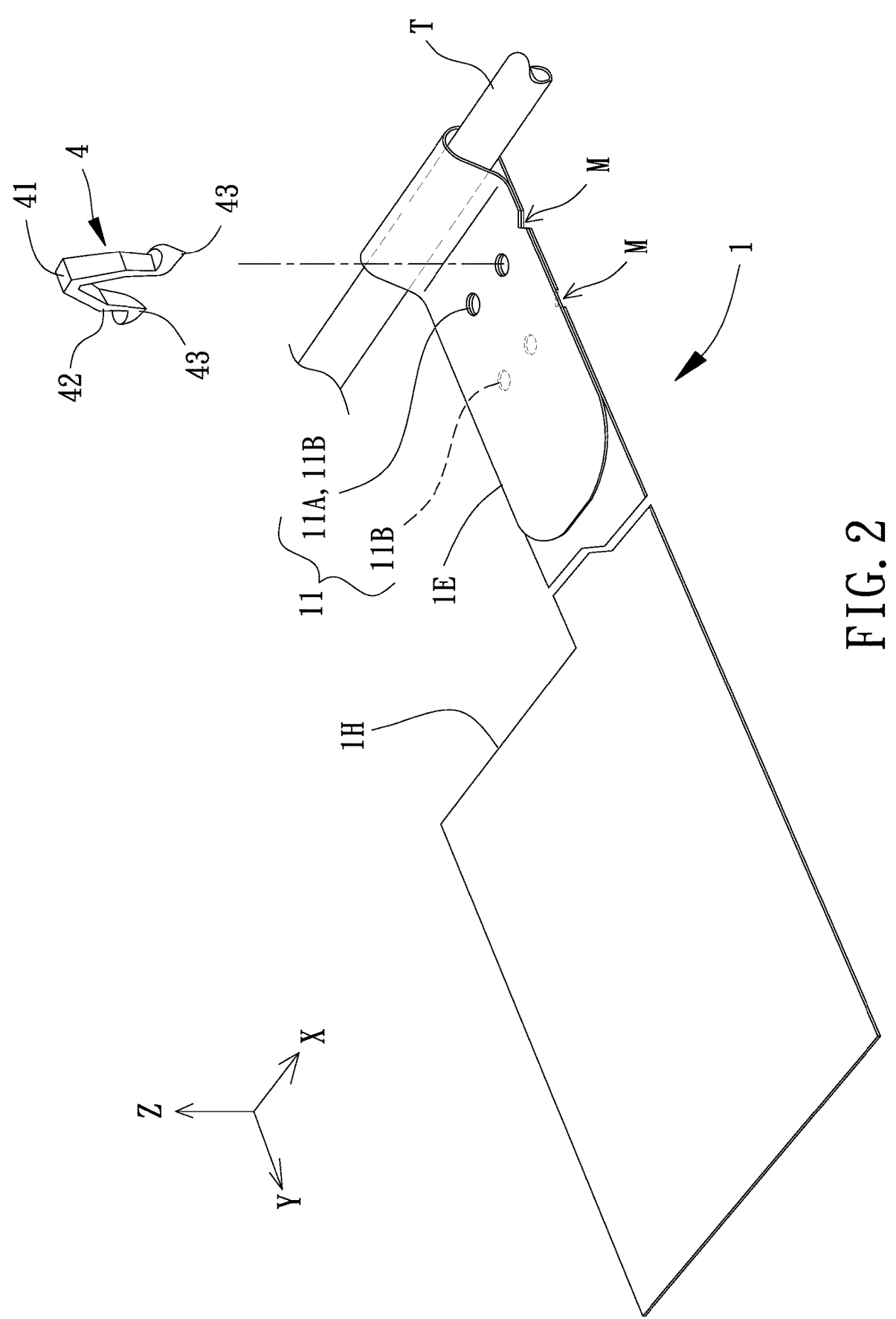
FIG. 2 is a diagrammatic view illustrating disposition of the signal sensing device of FIG. 1 around a to-be-sensed target.

FIGS. 1 and 2 show an example of a signal sensing device of a preferred embodiment according to the present invention and a to-be-sensed target surrounded by the signal sensing device. The signal sensing device includes a body 1 and a signal sensing element 2. A portion of the body 1 forms a surrounding portion configured to surround a to-be-sensed target T. The signal sensing element 2 is mounted in the body 1. Preferably, the to-be-sensed target T is an organ or a tissue of an organism. It is noted that the to-be-sensed target T shown in FIG. 2 is a blood vessel. Nevertheless, the to-be-sensed target T is not limited in this regard.

Optionally, the signal sensing device may further include a signal amplifying portion 3 disposed on the body 1. When a portion of the body 1 surrounds the to-be-sensed target T, the signal amplifying portion 3 is partially or entirely in contact with the to-be-sensed target T.

The body 1 is used to envelop the signal sensing element 2 to protect the signal sensing element 2 and to reduce the interference from the sensing environment to the signal sensing element 2. Optionally, the body 1 is in the form of a long strip and preferably has a wider area to surround the to-be-sensed target T. Optionally, the body 1 is a long strip and has a uniform size, such as in the length, width, and thickness. Optionally, as shown in FIGS. 1 and 2, the body 1 is a long strip and includes a head portion 1H and an extension portion 1E connected to the head portion 1H. The extension portion 1E extends outward from an end of the head portion 1H and has a length to surround the to-be-sensed target T by an entirety or a portion of the extension portion 1E. Particularly, a portion of the extension portion 1E forms an annular object to surround the to-be-sensed target T. When the extension portion 1E forms the annular object, a free end of the extension portion 1E or a portion near the free end may be fixed to a proper portion of the extension portion 1E per se, such that the body 1 may securely surround the to-be-sensed target T. The method for fixing the extension portion 1E may be selected according to the actual situation. The present invention is not limited in this regard.

As shown in FIG. 1, the number of the signal sensing element 2 is at least one. Each signal sensing element 2 incudes a signal transmission section 2a and a signal sensing section 2b in electrical connection with the signal transmission section 2a and is disposed in the body 1. In a case that a portion of the body 1 forms a surrounding portion which surrounds the to-be-sensed target T, a portion or an entirety of the signal transmission section 2a is located on the surrounding portion. Specifically, the signal transmission section 2a is located on the head portion 1H of the body 1 and may have an antenna structure to convert a sensing signal generated by the signal sensing section 2b (particularly a sensing signal generated in association with the to-be-sensed target T) into a transmission signal (such as an electromagnetic wave) having a specific working frequency. The transmission signal is sent out, particularly to a signal analysis device (not shown), and the transmission signal is converted into information to be monitored, permitting associated analysis or monitoring management. The signal sensing section 2b is located on the extension portion 1E of the body 1 and is distributed in an area of the body 1 which surrounds the to-be-sensed target T. The signal sensing section 2b receives to-be-monitored information (such as the blood flow rate) of the to-be-sensed target T (such as a blood vessel) and converts the to-be-monitored information into a sensing signal (such as an electric signal). Then, the signal sensing section 2b transmits the sensing signal to the signal transmission section 2a which generates an associated transmission signal. Specifically, the transmission signal may be transmitted to a corresponding receiving unit (not shown)

which may analyze the received transmission signal according to a predetermined approach and which may convert the transmission signal into the to-be-monitored information of the to-be-sensed target T, thereby observing, analyzing, or monitoring the change of the to-be-monitored information.

Preferably, the antenna structure is a flat antenna or planar antenna. The working frequency may be decided according to the antenna pattern of the signal transmission section 2a. Namely, given the same material and size, different working frequencies may be obtained via different antenna patterns. The antenna pattern may be comprised of at least one of a square loop, a circular loop, a triangular loop, a non-symmetric loop, and other patterns. According to research of the present invention, when the signal sensing device according to the present invention is mounted in a human body, a better transmission effect may be obtained when the working frequency is 350-450 MHz. Preferably, the working frequency is 401-406 MHz. Thus, in the above working frequency range, the signal transmission section 2a may proceed with signal transmission with a stable signal quality.

Optionally, as shown in FIG. 1, the body 1 further includes an assembling structure 11 having a first assembling portion 11A and a second assembling portion 11B. The number of each of the first assembling portion 11A and the second assembling portion 11B is at least one. Furthermore, the first assembling portion 11A and the second assembling portion 11B are spacedly disposed. In a case that plural first assembling portions 11A and/or plural second assembling portions 11B are used, the plural assembling portions (the first assembling portion 11A and/or the second assembling portion 11B) are spacedly disposed. Preferably, the first assembling portion 11A and the second assembling portion 11B are disposed on the extension portion 1E of the body 1. The first assembling portion 11A is closer to a free end of the extension 1E than the second assembling portion 11B.

Figures 3, 4:
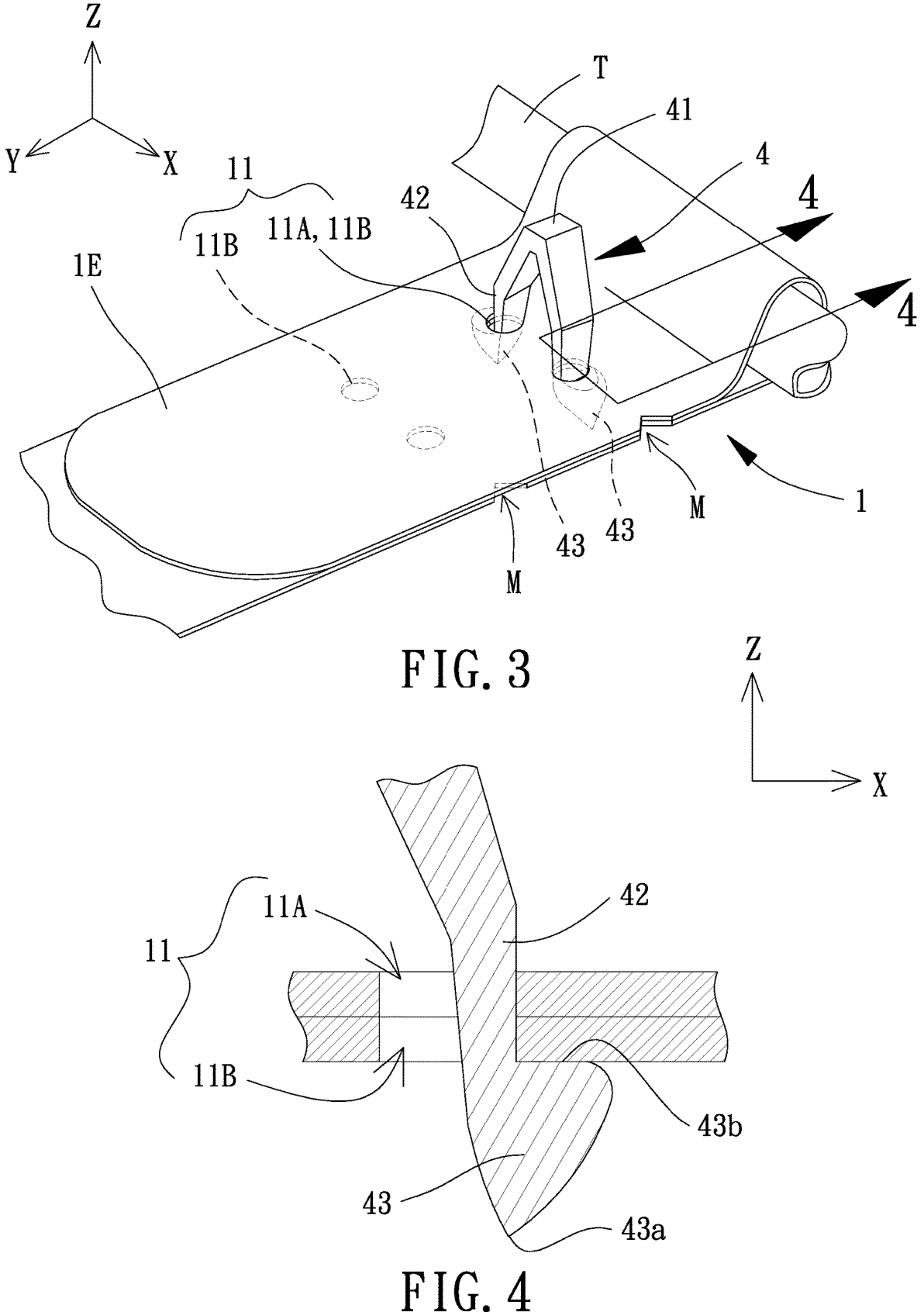
FIG. 3 is a diagrammatic perspective view illustrating fixing of the signal sensing of FIG. 2 on the to-be-sensed target.
FIG. 4 is a cross sectional view taken along section line 4-4 of FIG. 3.

As shown in FIGS. 2-3, in a case that the body 1 forms an annular structure, such as by bending, particularly the annular structure formed by the body 1 surrounds the to-be-sensed target T, the first assembling portion 11A and the second assembling portion 11B may be disposed to align with each other, particularly overlap and in contact with each other. At this time, to reliably maintain the alignment between the first assembling portion 11A and the second assembling portion 11B and to dispose and/or secure the body 1 around the to-be-sensed target T, a fastener 4 is provided to engage with the first assembling portion 11A and the second assembling portion 11B, thereby maintaining the shape of the annular portion. Specifically, the engagement means that the fastener 4, the first assembling portion 11A and the second assembling portion 11B have matching recessed features or protruding features in structure and can be achieved by, for example, the flexibility of one or more of snap-fit, structural tension, and mutual coupling features.

Optionally, each of the first assembling portion 11A and the second assembling portion 11B includes at least one through-hole. The fastener 4 includes a connecting portion 41, an insertion portion 42, and an engaging portion 43. The insertion portion 42 protrudes outward from the connecting portion 41 and includes a free end remote from the connecting portion 41. The engaging portion 43 protrudes outward from a portion of the insertion portion 42 and is spaced from the connecting portion 41 by a distance. Preferably, the engaging portion 43 protrudes from the free end of the insertion portion 42. When the fastener 4 is engaged with the first assembling portion 11A and the second assembling portion 11B, the insertion portion 42 extends through aligned through-holes of the first assembling portion 11A and the second assembling portion 11B, the connecting portion 41 is located on a side of one of the first assembling portion 11A and the second assembling portion 11B, and the engaging portion 43 is coupled with and abuts against a side of another of the first assembling portion 11A and the second assembling portion 11B.

Specifically, as shown in FIGS. 3 and 4, each through-hole has a diameter in a radial direction (such as on the X-Y plane) and extends in an axial direction (such as the extending direction of Z-axis). The connecting portion 41 is outside of the assembling structure 11 and extends beyond the through-hole in the radial direction, such that when the fastener 4 engages with the assembling structure 11, the connecting portion 41 will not pass through the through-hole and will be located on a side of the assembling structure 11 (namely, on a side of one of the first assembling portion 11A and the second assembling portion 11B). The insertion portion 42 extends in the axial direction. Furthermore, the shape or contour of the insertion portion 42 in the axial direction permits passage through the through-holes of the assembling structure 11. The engaging portion 43 includes an inlet end 43a and an engaging end 43b. The inlet end 43a is opposite to (remote from) the connecting portion 41. The engaging end 43b is located between the connecting portion 41 and the inlet end 43a. When the fastener 4 engages with the assembling structure 11, the engaging end 43b engages with and abuts against the other side of the assembling structure 11.

Preferably, the inlet end 43a expands gradually towards the engaging end 43b, such that the engaging portion 43 has gradually increasing lengths in the radial direction from the inlet end 43a towards the engaging end 43b in the axial direction. Thus, by the gradual increasing lengths of the engaging portion 43 in the radial direction, the inlet end 43a of the engaging portion 43 may be easily inserted into and pass through the aligned/overlapped through-holes of the first assembling portion 11A and the second assembling portion 11B. After the engaging portion 43 passes through the through-holes, the engaging end 43b extends beyond the through-holes in the radial direction. Therefore, after the engaging portion 43 passes through the through-holes, the connecting portion 41 is located on a side of the assembling structure 11, whereas the engaging end 43b engages with and abuts against the other side of the assembling structure 11. Furthermore, since both the connecting portion 41 and the engaging end 43b extend beyond the through-holes in the radial direction, the first assembling portion 11A and the second assembling portion 11B are inseparably engaged to assure that the signal sensing device according to the present invention can securely surround the to-be-sensed target T.

According to the description of the assembling structure 11 and the fastener 4, the number of the through-hole may be one or more in the present invention. Furthermore, the dispositions of the through-holes of the first assembling portion 11A and the through-holes of the second assembling portion 11B in number, position, and shape may be designed to correspond to each other. Furthermore, with respect to the disposition of the through-holes, the fastener 4 has correspondingly disposed insertion portion 42. In a preferred embodiment according to the present invention, as shown in FIGS. 1-4, each of the first assembling portion 11A and the second assembling portion 11B has two through-holes, and the fastener 4 includes two insertion portions 42 associated with the number of the through-holes and in the form of protruding structures, such that the fastener 4 is substantially U-shaped or V-shaped. It is noted that although the number of through-holes of each of the first assembling portion 11A and the second assembling portion 11B is two, the present invention is not limited in this regard.

Optionally, as shown in FIGS. 1-3, the body 1 may further include a plurality of marked features M disposed on the body 1 and aligned with the first assembling portion 11A and the second assembling portion 11B to mark/indicate the positions of the first assembling portion 11A and the second assembling portion 11B. Each of the plurality of marked features M is a notch, preferably a triangular notch. More preferably, each triangular notch has a vertex aligned with an associated one of the first assembling portion 11A and the second assembling portion 11B.

Figure 5:
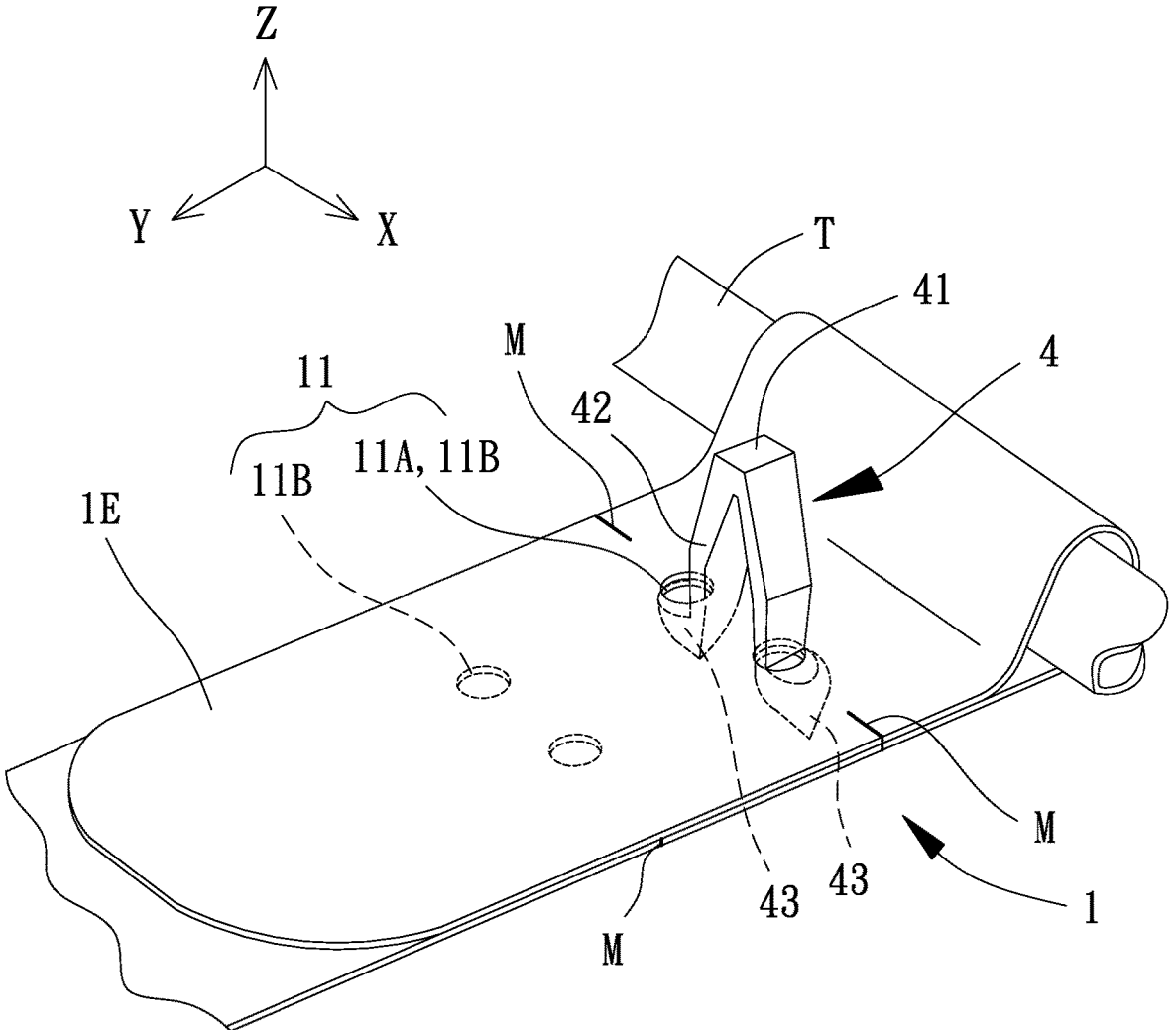
FIG. 5 is a diagrammatic view illustrating another example of marked features of the signal sensing device according to the present invention.

Optionally, as shown in FIG. 5, each of the plurality of marked features M is a line-type mark, preferably a straight-line mark. Optionally, the straight-line mark may extend to a side of the body 1 or may be merely disposed on a side of the body 1, such that when the first assembling portion 11A is aligned with the second assembling portion 11B, the straight-line mark on the first assembling portion 11A and the straight-line mark on the second assembling portion 11B are aligned on a side of the body 1. The side of the body 1 refers to at least one of two lateral sides of the body 1 in the width direction, or at least one of two lateral sides spaced from each other along X axis, or at least one of two lateral sides of the surrounding portion opposite to each other in the axial direction when the body 1 forms the surrounding portion. Particularly, the marked features M for alignment are on the same side of the body 1.

By the provision of the marked features M, an indication of alignment of the first assembling portion 11A and the second assembling portion 11B is provided when the marked features M on the first assembling portion 11A are aligned with the marked features M on the second assembling portion 11B, such as the notches overlap with each other (as shown in FIGS. 1-3) or the line-type marks form a specific pattern (as shown in FIG. 5). Thus, when the user is mounting the signal sensing device according to the present invention on a to-be-sensed target T, the marked features M permits easier alignment of the first assembling portion 11A and the second assembling portion 11B, thereby fixing the body 1 on the to-be-sensed target T.

It is noted that the marked features M are marks which are visually distinct from the body 1 (particularly distinct from the body 1 and the to-be-sensed target T), such as one of or a combination of colors, characters, symbols, figures, markings, and structural dispositions (such as protrusions or notches) which form an indicative or distinguishable feature. Therefore, the marked features M are not limited to the notches (as shown in FIGS. 1-3) and line-type marks (as shown in FIG. 5).

Figure 6:
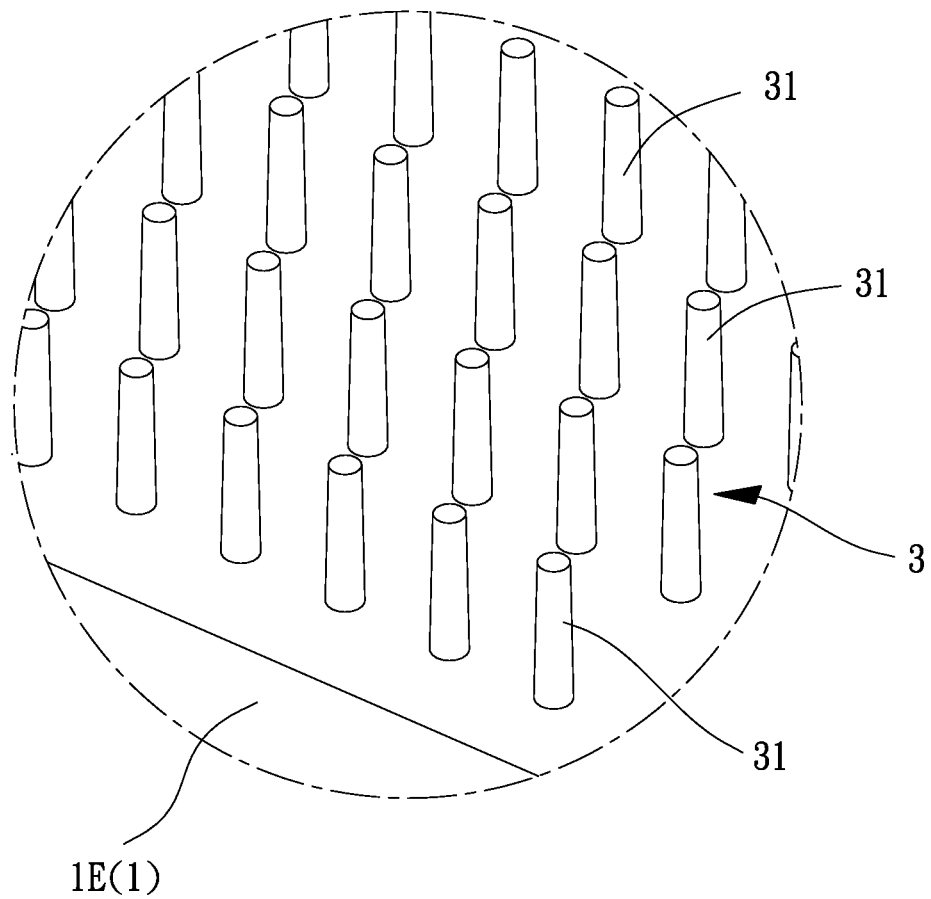
FIG. 6 is an enlarged view of a portion of the signal sensing device of FIG. 1.

In an embodiment of the signal sensing device having the signal amplifying portion 3, as shown in FIGS. 1, 2, and 6, the signal amplifying portion 3 has a plurality of protruding structures 31 protruding outward from an outer side of the body 1 to form a plurality of protrusive shapes. In a case that a portion of the body 1 forms a surrounding portion which surrounds the to-be-sensed target T, a portion or an entirety of the signal amplifying portion 3 is located on the surrounding portion, and the signal amplifying portion 3 is partially or entirely in contact with the to-be-sensed target T. Specifically, when the signal sensing device according to the present invention is in an extended state placed on a plane, as shown in FIG. 1, the plurality of protruding structures 3 protrudes in a direction away from the body 1. Particularly, the signal amplifying portion 3 protrudes from the extension portion 1E of the body 1 and is aligned with the signal sensing section 2b of the signal sensing element 2, such that when the body 1 surrounds the to-be-sensed target T, a portion or all of the plurality of protruding structures 31 of the signal amplifying portion 3 are in contact with the to-be-sensed target T, such that the signal amplifying portion 3 can contact with the to-be-sensed target T more closely, thereby enhancing the strength of the sensing signal (associated with the to-be-monitored information) received by the signal sensing section 2b. Optionally, each of the plurality of protruding structures 31 may be cylindrical, semi-circular, semi-elliptic, or trapezoidal in cross section. However, the shapes of the cross sections of the protruding structures 31 are not limited in this regard.

Preferably, when the plurality of protruding structures 31 is in contact with the to-be-sensed target T, the plurality of protruding structures 31 is partially or entirely pressed in the to-be-sensed target T. Particularly, the press in refers to a situation that the to-be-sensed target T is softer than the plurality of protruding structures 31, and in response to the body 1 (surrounding the to-be-sensed target T) turning from loose into tight, each of the plurality of protruding structures 31 in contact with the to-be-sensed target T will make the depressions in the contacted area of the to-be-sensed target T turn from shallow into deep. It is noted that the press in preferably does not adversely affect the normal function of the to-be-sensed target T and does not damage the to-be-sensed target T. Therefore, by partially or entirely pressing plurality of protruding structures 31 in the to-be-sensed target T, the contact area between the signal amplifying portion 3 and the to-be-sensed target T can be increased, thereby enhancing the strength of the sensing signal (associated with the to-be-monitored information) received by the signal sensing section 2b.

According to the above-mentioned structure disposition of the signal sensing device according to the present invention, the overall signal sensing device (particularly the entirety) may be made of biodegradable material, especially the material approved by the Food and Drug Administration (FDA) of the United States. Therefore, the signal sensing device is particularly suitable for installation in a target organism and can degrade in a predetermined period of time without the need of removal by operation, thereby avoiding the risk caused by the second operation. As an example, the predetermined period of time is 3-26 weeks, preferably 13-26 weeks. However, the predetermined period of time may permit a change in the material, thickness, etc. during the actual period required for monitoring. Thus, the predetermined period of time should not be limited to the period of time in the above examples.

In a specific application example, the signal sensing device may be embedded in a human body to measure a blood flow rate (corresponding to the to-be-monitored information) of a blood vessel (corresponding to the to-be-sensed target T). With regard to the biodegradable material, the body 1 and the insulating material 1 may be comprised of at least one of polyhydroxybutyrate (PHB), polyhydroxyvalerate (PHV), and poly-L-lactic acid (PLLA). The signal sensing element 2 may be comprised of a biodegradable metal, preferably magnesium. The signal amplifying portion 3 may be polycaprolactone (PCL). The fastener 4 may be selected from polydioxanone and L-lactide glycolide polymers. With regard to the disposition of the size of the overall device, as shown in FIG. 1, the head portion 1H of the body 1 has a length $L_H$ and a width $W_H$. Both the length $L_H$ and the width $W_H$ are 5-35 mm, preferably 10-30 mm, and more preferably 15-20 mm. The head portion 1H further has a thickness $T_H$ of 50-350 μm. The extension portion 1E has a width $W_E$ of 2-15 mm, preferably 5-10 mm, and a thickness $T_E$ of 50-350

μm. Furthermore, the length $L_E$ of the extension portion 1E is disposed according to the actual need. In association with the length, width, and thickness/height of the body 1, the thickness of each of the signal transmission section 2a and the signal sensing section 2b of the signal sensing element 2 is 5-100 μm, preferably 10-50 μm, and more preferably 10-15 μm. Regarding the size disposition of the length and width of the signal transmission section 2a and the signal sensing section 2b, the signal transmission section 2a and the signal sensing section 2b are respectively disposed in association with the head portion 1H and the extension portion 1E of the body 1. Particularly, the lengths and widths of the signal transmission section 2a and the signal sensing section 2b are smaller than those of the head portion 1H and the extension portion 1E, such that the signal sensing elements 2 can be mounted in the body 1. The diameter of each through-hole of the first assembling portion 11A and the second assembling portion 11B is 10-30% of the width $W_E$ of the extension portion 1E, preferably 15-25%, and more preferably 20%. The spacing between the two through-holes of the first assembling portion 11A and between the two through-holes of the second assembling portion 11B is 1.5-6 times (preferably 1.5-3 times, and more preferably 1.5-2 times) the diameter of the through-hole. The sum of the diameters of the through-holes and the spacing between the through-holes must be smaller than the width $W_E$ of the extension portion 1E.

In a practical embodiment, the length, width, and height of each of the plurality of protruding structures 31 of the signal amplifying portion 3 is 0.1-500 μm. Particularly, according to the research of the present invention, the sensed signal is significantly enhanced when the plurality of protruding structures 31 is cylindrical. Specifically, in the disposition of the cylindrical protruding structures 31, each of the plurality of protruding structures 31 has a diameter of 10-500 μm (preferably 250-400 μm, and more preferably 300-350 μm) and a height of 1.5-100 μm (preferably 40-75 μm, and more preferably 50 μm). Each two protruding structures 31 have a spacing between the centers thereof, and the spacing is 1.5-5 times the diameter, preferably 2-3.5 times the diameter.

Figure 7:
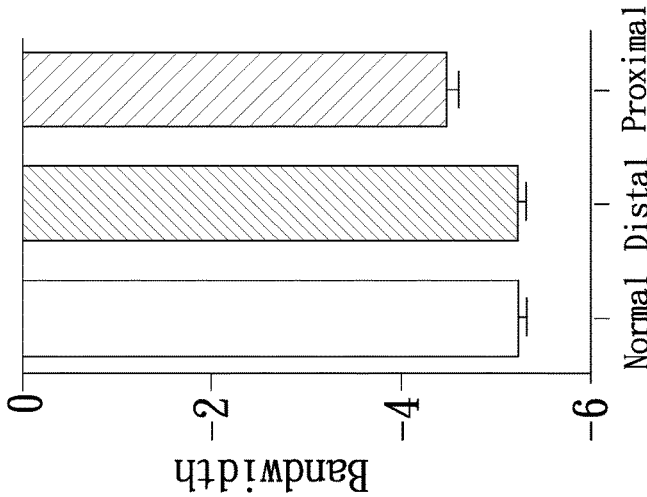
FIG. 7 is a diagrammatic view illustrating signal characteristics of a vein sensed by the signal sensing device according to the present invention.
Figure 7:
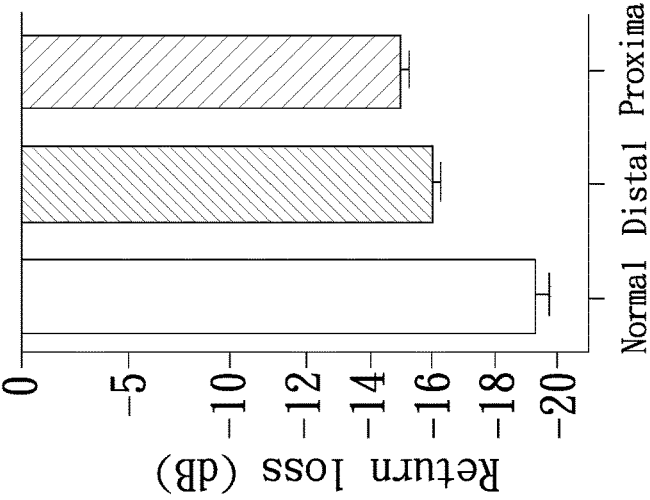
Figure 7:
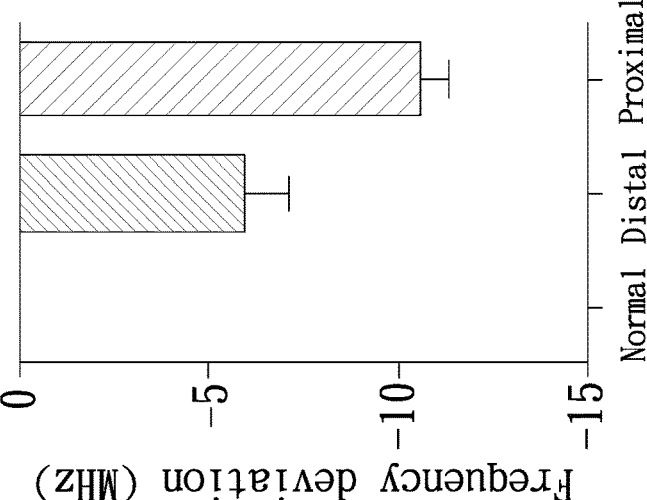

It is noted that based on the shape and size of the protruding structures 31 according to the present invention, when the signal sensing device according to the present invention is used to measure the blood signal of an artery or a vein, particularly used to measure the vein signal, no matter the blood vessel is during the period of vasoconstriction or relaxation, a trend of change in the blood flow rate can still be obtained stably. Specifically, FIG. 7 illustrates the signal characteristics of a vein (the to-be-sensed target T) of an organism, with the vein surrounded and measured by the signal sensing device having the plurality of protruding structures 31 according to the present invention. Furthermore, a proximal blood vessel signal, a distal blood vessel signal, and a normal blood vessel signal can be measured. The term "proximal blood vessel signal" refers to a signal obtained in a situation in which a blood vessel clamp (not shown) is installed on the vein measured, such that the blood flow rate at a location downstream the clamped position is reduced (reducing the signal strength), and the signal sensing device is mounted downstream the clamped position and is spaced from the blood vessel clamp by about 5 mm. The term "distal blood vessel signal" refers to a signal obtained in a situation in which the signal sensing device is mounted downstream the clamped position and is spaced from the blood vessel clamp by about 10 mm. The term "normal blood vessel signal" refers to a signal obtained in a situation in which no blood vessel clamp is used, such that the vein measured by the signal sensing device is in a natural state. By contrast, in a comparison experiment (published by Stanford University) using pyramidal protruding structures, and the optimal size is 50 μm at the base (the maximal side) of the pyramidal protruding structure, and the minimal spacing between the edges of the protruding structures is 40 μm. However, the comparison experiment can only measure the change in the blood flow rate of an artery. Vein is the most common site of thrombus formation after surgery. Therefore, the blood signal of the vein needs to be highly monitored. However, the blood flow fluctuation/signal of a vein is smaller than that of an artery and is, thus, difficult to measure. Therefore, the present invention is a breakthrough to the comparison experiment limited to the measurement of an artery, such that the measured signal has a higher reference value. Specifically, the present invention simulates a thrombus situation of a vein by using a blood vessel clamp, and the signal sensing device according to the present invention can still measure the corresponding blood flow signal to reflect the change in the blood flow of the monitored blood vessel, which significantly increases the applications of the blood vessel signal monitoring. Furthermore, it is noted that the experiment according to the present invention is conducted on a vein of a living animal (such as a rabbit). Particularly, although the diameter of the vein of the experimental living body is smaller than that of a human body, the signal sensing device according to the present invention can still obtain readable signals with a stable quality, which further proves excellent performance on the effects of signal transmission and sensing.

In view of the foregoing, the signal sensing device according to the present invention can be fixed on the to-be-sensed target through disposition of the assembling structure which can engage with a fastener. Furthermore, by the disposition of the marked features, easier alignment of the assembling structure can be achieved. By the provision of the protruding structures of the signal amplifying portion protruding from the extension portion of the body and aligned with the signal sensing section of the signal sensing element also located on the extension portion of the body, the strength of the sensing signal (associated with the to-be-monitored information) received by the signal sensing section can be enhanced. Furthermore, by the provision of the cylindrical protruding structures having a diameter of about 250-400 μm (preferably 300-350 mm) and a height of about 40-75 μm, the sensing signal strength can be further enhanced. Furthermore, by the size disposition of the body, the signal sensing element, and the signal amplifying portion, the signal sensing device is suitable for sensing signals of a specific internal organ or tissue of an organism (particularly a human body). Furthermore, the overall signal sensing device according to the present invention may be made of a biodegradable material, and by the disposition of the overall size, the signal sensing device is suitable for installation in the human body to sense the interested signal and can degrade completely in a predetermined period of time without the need of removal by operation, thereby avoiding the risk caused by the second operation.

Although the present invention has been described with respect to the above preferred embodiments, these embodiments are not intended to restrict the present invention. Various changes and modifications on the above embodiments made by any person skilled in the art without departing from the spirit and scope of the present invention are still within the technical category protected by the present invention. Accordingly, the scope of the present invention shall include the literal meaning set forth in the appended claims and all changes which come within the range of equivalency of the claims.

What is claimed is:

1. A signal sensing device comprising:
   a body comprising a surrounding portion configured to surround a to-be-sensed target;
   a signal sensing element disposed in the body and including a signal transmission section and a signal sensing section in electrical connection with the signal transmission section, wherein the signal sensing section is at least partially located on the surrounding portion; and
   a signal amplifying portion configured to be at least partially in contact with the to-be-sensed target and having a plurality of protruding structures protruding outward from the body, wherein each of the plurality of protruding structures is cylindrical and has a diameter of 250-400 μm and a height of 40-75 μm.

2. The signal sensing device as claimed in claim 1, wherein the diameter of each of the plurality of protruding structures is 300-350 μm, and wherein the height of each of the plurality of protruding structures is 50 μm.

3. The signal sensing device as claimed in claim 1, wherein the body includes a head portion and an extension portion connected to the head portion, wherein the extension portion extends outward from an end of the head portion and has a length configured to surround the to-be-sensed target by an entirety or a portion of the extension portion.

4. The signal sensing device as claimed in claim 3, wherein the signal transmission section is disposed on the head portion of the body and includes an antenna structure, wherein the signal sensing section is disposed on the extension portion of the body, and wherein the signal amplifying portion protrudes from the extension portion of the body and is aligned with the signal sensing section of the signal sensing element.

5. The signal sensing device as claimed in claim 4, wherein the head portion of the body has a length and a width both of which are 5-35 mm, wherein the extension portion has a width of 2-15 mm, wherein each of the head portion and the extension portion has a thickness of 50-350 μm, and
   wherein each of the signal transmission section and the signal sensing section has a thickness of 10-100 μm.

6. The signal sensing device as claimed in claim 5, wherein both the length and the width of the head portion of the body are 10-30 mm, and wherein the width of the extension portion is 5-10 mm.

7. The signal sensing device as claimed in claim 3, wherein both a length and a width of the head portion of the body are 15-20 mm.

8. The signal sensing device as claimed in claim 1, wherein the body further includes an assembling structure having a first assembling portion and a second assembling portion which are spaced from each other and which are disposed on the body, and wherein when the surrounding portion surrounds the to-be-sensed target, the first assembling portion and the second assembling portion are aligned with each other.

9. The signal sensing device as claimed in claim 8, further comprising a fastener, wherein when the first assembling portion and the second assembling portion are aligned with each other, the fastener is engaged with the first assembling portion and the second assembling portion to maintain a shape of the surrounding portion.

10. The signal sensing device as claimed in claim 9, wherein each of the first assembling portion and the second assembling portion includes at least one through-hole, wherein the fastener includes a connecting portion, at least one insertion portion, and at least one engaging portion, wherein the at least one insertion portion protrudes outward from the connecting portion, wherein the at least one engaging portion protrudes outward from the at least one insertion portion, wherein when the fastener is engaged with the first assembling portion and the second assembling portion, the at least one insertion portion extends through aligned through-holes of the first assembling portion and the second assembling portion, the connecting portion is located on a side of one of the first assembling portion and the second assembling portion, and the at least one engaging portion engages with and abuts against a side of another of the first assembling portion and the second assembling portion.

11. The signal sensing device as claimed in claim 10, wherein the at least one through-hole of each of the first assembling portion and the second assembling portion has a diameter in a radial direction, wherein the at least one engaging portion includes an inlet end and an engaging end, wherein the inlet end is opposite to the connecting portion, wherein the engaging end is located between the connecting portion and the inlet end, wherein the inlet end expands gradually towards the engaging end, such that the at least one engaging portion has gradually increasing lengths in the radial direction from the inlet end towards the engaging end in an axial direction perpendicular to the radial direction.

12. The signal sensing device as claimed in claim 10, wherein the at least one through-hole of each of the first assembling portion and the second assembling portion has two through-holes, and wherein the at least one insertion portion of the fastener includes two insertion portions, such that the fastener is substantially U-shaped or V-shaped.

13. The signal sensing device as claimed in claim 8, wherein the body further includes a plurality of marked features disposed on the body and aligned with the first assembling portion and the second assembling portion.

14. The signal sensing device as claimed in claim 13, wherein each of the plurality of marked features is a triangular notch having a vertex aligned with an associated one of the first assembling portion and the second assembling portion.

15. The signal sensing device as claimed in claim 13, wherein each of the plurality of marked features is a line-type mark.

16. The signal sensing device as claimed in claim 1, wherein the signal sensing device is made of one or more bio-degradable materials.

* * * * *